United States Patent
Zheng et al.

(10) Patent No.: US 10,993,926 B2
(45) Date of Patent: May 4, 2021

(54) USE OF IDHP IN PREPARATION OF DRUG OR HEALTH PRODUCT FOR PREVENTION AND TREATMENT OF CORONARY ATHEROSCLEROSIS DISEASE

(71) Applicant: NORTHWEST UNIVERSITY, Shaanxi (CN)

(72) Inventors: Xiaohui Zheng, Shaanxi (CN); Yajun Bai, Shaanxi (CN); Pu Jia, Shaanxi (CN); Yajun Zhang, Shaanxi (CN); Sha Liao, Shaanxi (CN)

(73) Assignee: NORTHWEST UNIVERSITY, Shaanxi (CN)

( * ) Notice: Subject to any disclaimer, the term of this patent is extended or adjusted under 35 U.S.C. 154(b) by 214 days.

(21) Appl. No.: 16/338,801

(22) PCT Filed: Sep. 29, 2017

(86) PCT No.: PCT/CN2017/104278
§ 371 (c)(1),
(2) Date: Apr. 2, 2019

(87) PCT Pub. No.: WO2018/064953
PCT Pub. Date: Apr. 12, 2018

(65) Prior Publication Data
US 2020/0038357 A1    Feb. 6, 2020

(30) Foreign Application Priority Data
Oct. 8, 2016   (CN) .......................... 201610876752.3

(51) Int. Cl.
A61K 31/21    (2006.01)
A61K 31/216   (2006.01)
A23L 29/00    (2016.01)
A61P 7/02     (2006.01)
A61P 9/10     (2006.01)
A61P 25/28    (2006.01)

(52) U.S. Cl.
CPC .......... *A61K 31/216* (2013.01); *A23L 29/035* (2016.08); *A61P 7/02* (2018.01); *A61P 9/10* (2018.01); *A61P 25/28* (2018.01)

(58) Field of Classification Search
CPC .................................................... A61K 31/216
See application file for complete search history.

(56) References Cited

FOREIGN PATENT DOCUMENTS

| CN | 1583710 A   | 2/2005  |
|----|-------------|---------|
| CN | 106420688 A | 2/2017  |
| EP | 1437137 A   | 9/2002  |
| WO | 9735579     | 10/1997 |

OTHER PUBLICATIONS

International Search Report corresponding to Application No. PCT/CN2017/104278; dated Dec. 27, 2017.
Jing-jing Shu et al., "Progress on the pharmacological actions and mechanism of Danshensu," Journal of Pharmaceutical Practice, vol. 30, No. 4, Jul. 25, 2012 with English Translated title and abstract.
Jingwei Tian et al., "ND-309, a novel compound, ameliorates cerebral infarction in rats by antioxidant action," School of Pharmacy, Neuroscience Letters 442, 2008, pp. 279-283.
Xin Gu, "The Asymmetric Synthesis and Pharmacological Studies of Danshensu and its Derivatives," Shaanxi University of Science and Technology, May 2015.
EPO Extended Search Report for corresponding EP17857834.0 dated Apr. 24, 2020.
Wang et al: "Vasorelaxant effect of isopropyl 3-(3,4-di hydroxyphenyl )-2-hydroxypropanoate, a novel metabolite from Salvia miltiorrhiza, on isolated rat mesenteric artery", European Journal of Pharmacology, Elsevier Science, NL, vol. 579, No. I-3, Oct. 13, 2007, pp. 283-288.
Qian Yin et al: "A metabolite of Danshen formulae attenuates cardiac fibrosis induced by isoprenaline, via a N0X2/R0S/p3B pathway: IDHP protects against cardiac fibrosis via N0X2", British Journal of Pharmacology, vol. 172, No. 23, 5 May 5, 2015; pp. 5573-5585.
Sha0-Xia Wang: "Anti-Inflammatory Effects of Isopropyl 3-(3, 4-Di hydroxyphenyl)-2-Hydroxypropanoate, a Novel Metabolite from Danshen, on Activated Microglia", Chinese Journal of Physiology, vol. 55, No. 6, Dec. 31, 2012, pp. 428-443.
Dong et al., "Asymmetric synthesis and biological evaluation of Danshensu derivatives as anti-myocardial ischemia drug candidates", Bioorganic & Madicinal Chemistry, vol. 17, 2009, pp. 3499-3507.
First Examination Report corresponding to Indian counterpart application No. 201917017111; dated Jan. 31, 2020.
Kashiwazaki, MD, et al. "Involvement of circulating endothelial progenitor cells in carotid plaque growth and vulnerability", J Neurosurg, vol. 125, Dec. 2016, pp. 1549-1556.
Zhang et al., "In Vivo Angiogenesis Screening and Mechanism of Action of Novel Tanshinone Derivatives Produced by One-Pot Combinatorial Modification of Natural Tanshinone Mixture from Salvia Miltiorrhiza", PLoS One, Jul. 2014, vol. 9, issue 7, e100416. doi:10.1371/journal.pone.0100416; 15 pages.

*Primary Examiner* — Shawquia Jackson
(74) *Attorney, Agent, or Firm* — Cantor Colburn LLP (57) ABSTRACT

Use of isopropyl β-(3,4-dihydroxyphenyl)-α-hydroxypropionate (IDHP) in the preparation of a drug or a health product for prevention and treatment of coronary atherosclerosis diseases. The IDHP can also be used to inhibit platelet aggregation, to promote angiogenesis, and to prepare a drug and a health product for prevention and treatment of senile vascular dementia.

9 Claims, 6 Drawing Sheets

USE OF IDHP IN PREPARATION OF DRUG OR HEALTH PRODUCT FOR PREVENTION AND TREATMENT OF CORONARY ATHEROSCLEROSIS DISEASE

CROSS REFERENCE TO RELATED APPLICATIONS

This is the U.S. national stage of application No. PCT/CN2017/104278, filed on Sep. 29, 2017. Priority under 35 U.S.C. § 119(a) and 35 U.S.C. § 365(b) is claimed from Chinese Application No. 201610876752.3, filed Oct. 8, 2016; the disclosures of which are incorporated herein by reference.

FIELD

The present disclosure relates to a new use of β-(3,4-dihydroxyphenyl)-α-hydroxyisopropyl propionate (IDHP), in particular to the use of IDPH for the manufacture of a medicament or healthcare food in prevention and treatment of diseases related to coronary artery atherosclerosis.

BACKGROUND

β-(3,4-Dihydroxyphenyl)-α-hydroxyisopropyl propionate (IDHP) is an active compound screened from a large number of metabolites and their series of modifications during the research on Danshen Dripping Pills, Guanxin Danshen Tablets, Danshen Drink and other compound Danshen prescriptions, and Jun-Shi pair herbs by using HPLC-MS, GC-MS, GC-FTIR, MS, NMR and other technical methods of metabolomics technology. IDHP can also be synthesized.

SUMMARY

The inventors explored the role of IDHP in inhibiting platelet aggregation, promoting angiogenesis, etc., which provided a valuable theoretical basis for development of new drugs and healthcare foods for prevention and treatment of coronary atherosclerosis-related diseases.

Coronary artery atherosclerosis is a type of disease caused by the buildup of plaque inside coronary artery that cause stenosis or obstruction of the vascular lumen, resulting in ischemia, hypoxia or necrosis. Common coronary atherosclerosis-related disease is coronary heart disease, stroke and myocardial infarction (MI). The major pathogenesis of coronary heart disease is closely related to the unstable coronary atherosclerotic plaque and the formation of thrombosis. Platelet aggregation is an important factor resulting in thrombosis, so antiplatelet therapy plays an important role in the prevention and treatment of coronary heart diseases. Stroke refers to a high-risk disease that, for a patient with cerebrovascular disease, various factors will induce cerebral artery stenosis, occlusion or rupture, resulting in acute cerebral circulation dysfunction, and clinically manifested as transient or permanent brain dysfunction. Antiplatelet therapy plays an important role in the primary and secondary prevention of stroke, and is currently recognized as one of the three major treatments (surgery, anticoagulation and antiplatelet aggregation). In addition, the occurrence and treatment of coronary artery atherosclerosis-related diseases are closely related to angiogenesis. Pathological neovascularization often occurs in atherosclerotic plaques, which can promote the development of atherosclerotic lesions, and even induce plaque hemorrhage and plaque rupture and its complications. The density of neovascularization around the infarction site of ischemic stroke is directly related to the survival rate of patients with ischemic stroke, and promoting angiogenesis after ischemic stroke is conducive to saving the ischemic penumbra. Angiogenesis is also a key process in coronary reperfusion and ischemic myocardium repair. In addition, pro-angiogenesis plays a significant role after recovery from myocardial infarction. The inventors' studies show that IDHP can significantly inhibit ADP or collagen-induced human platelet aggregation, and at the same time, IDHP can significantly promote angiogenesis in primary human umbilical vein endothelial cells (HUVEC). This result indicates that IDHP can be used to prepare drugs for prevention and treatment of diseases related to coronary artery atherosclerosis.

The inventors found that IDHP can significantly inhibit ADP or collagen-induced human platelet aggregation, which becomes a basis for using IDHP in the development of anti-platelet aggregation drugs.

The inventors found that IDHP can significantly promote angiogenesis in primary human umbilical vein endothelial cells (HUVEC), and IDHP can also significantly promotes the growth of zebrafish intersegmental vessels and posterior longitudinal blood vessels, which indicates that IDHP can be used to prepare drugs for promoting angiogenesis.

IDHP can significantly inhibit human platelet aggregation and promote angiogenesis, improve blood circulation, and thereby can be used to treat vascular dementia.

By acute and chronic toxicity tests and hemolysis experiments in mice, the inventors found that the safety of IDHP is relatively high. In combination with the above activity findings, IDHP can be used to develop healthcare foods for preventing and treating coronary artery atherosclerosis, anti-platelet aggregation, promoting angiogenesis, and preventing and treating vascular dementia.

The inventors found that IDHP is a human body-derived substance. By intaking IDHP, the balance state of the body can be regulated, to achieve the purpose of prevention and treatment of coronary atherosclerosis-related diseases and vascular dementia.

DETAILED DESCRIPTION

The structure of IDHP compound of the present disclosure is as shown in the following formula, and the preparation method thereof can be referred to CN 200410026205.3, but is not limited to the description of the literature.

IDHP

The healthcare foods mentioned in the present disclosure may be a soft capsule, a dropping pill, an emulsion, a tablet, a spray, etc.

Figure 1:
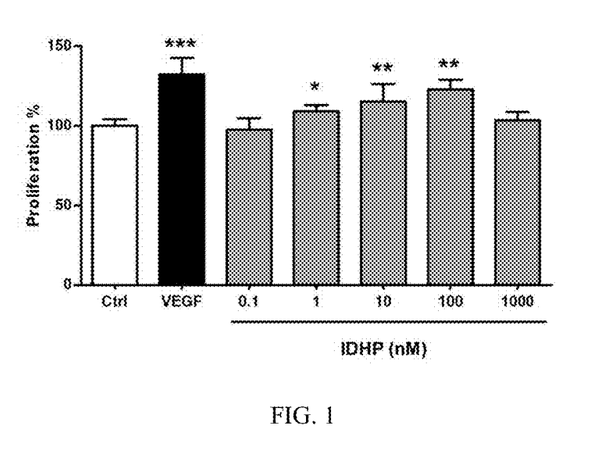
FIG. 1 shows the effect of different concentrations of IDHP on the proliferation of human umbilical vein endothelial cells.

Example 1: IDHP Promotes Angiogenesis of Cultured Human Umbilical Vein Endothelial Cells (HUVEC) In Vitro 1.1 Detect Proliferation of Human Umbilical Vein Endothelial Cells Promoted by IDHP—CCK-8 Method Human umbilical vein endothelial cells were seeded in a 96-well plate at a density of approximately 2,500 cells per well. After the cells were culture for 24 hours, the medium was changed for a fresh medium containing drug, 100 μl/well, and the cells were continued culturing for 48 hours. 2 hours before the end of drug treatment, CCK-8 reagent was added to the culture medium in the dark, 10 μl per well. The culture was continued for 2 hours, and then the absorbance at 450 nm was determined with a microplate reader to calculate the cell proliferation rate. The result is shown in FIG. 1. Compared with the blank control group, IDHP significantly promoted the proliferation of vascular endothelial cell at a concentration of $10^{-9}$ to $10^{-7}$ M (P<0.01).

Figure 2:
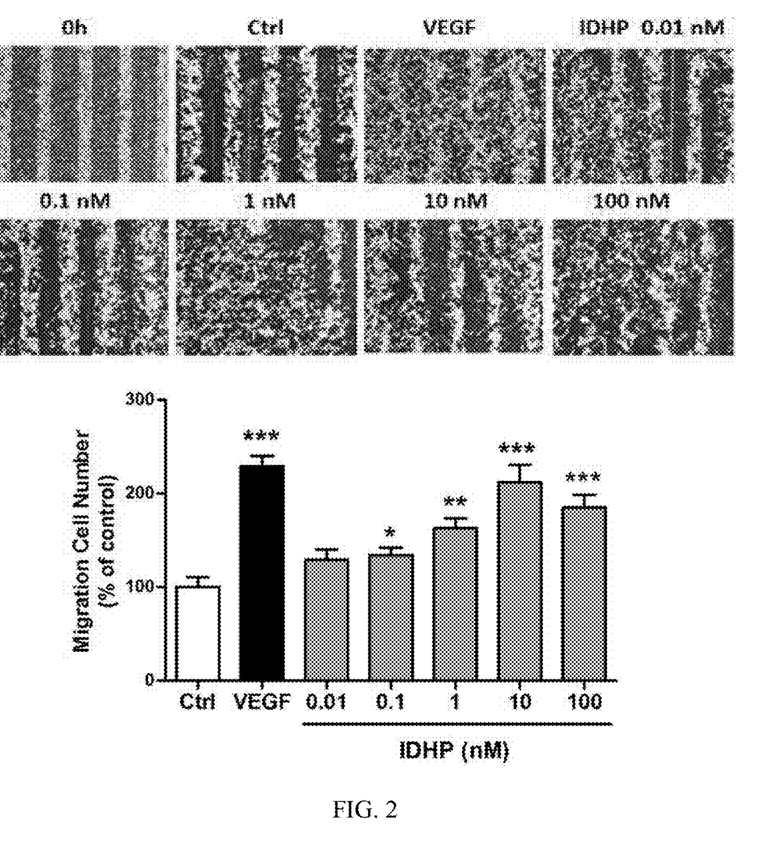
FIG. 2 shows the effect of different concentrations of IDHP on the migration of human umbilical vein endothelial cells.

1.2 Detect Migration of Human Umbilical Vein Endothelial Cells (HUVEC) Promoted by IDHP—Scratch Method Endothelial cells were seeded on a cover slip pre-coated with gelatin in a 24-well plate at a density of about $10^5$ cells per well. After the cells attached to the cover slip and reached confluence, cells were starved in a medium without serum for 4 hours. A home-made tool was used to make scratch on the cover slip with cells. The cover slip was washed twice with PBS, and a medium containing drug was added, 600 μl/well. Control group was immediately fixed with ice-cold methanol at zero time point; rest of the cells were cultured for 16 hours, and then fixed with ice-cold methanol. Images were acquired under a microscope and subjected to statistics analysis. The result (FIG. 2) shows that IDHP could promote the migration of human umbilical vein endothelial cells (HUVEC) in a dose-dependent manner at a concentration range of $10^{-10}$ to $10^{-7}$ M.

Figure 3:
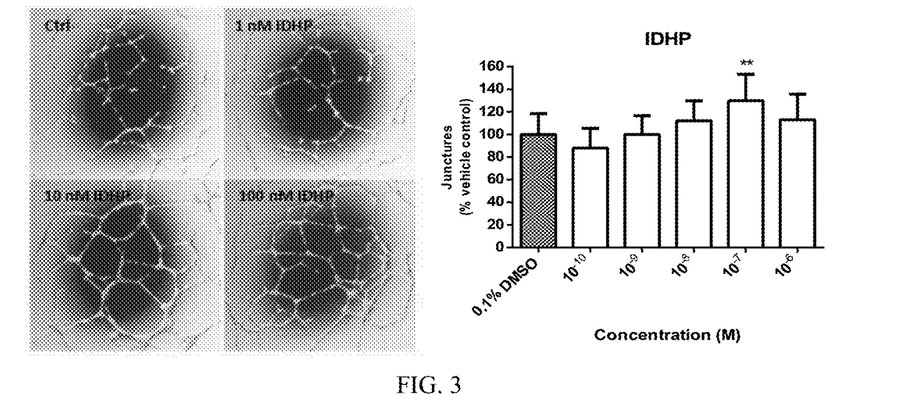
FIG. 3 shows the effect of different concentrations of IDHP on the tube formation of human umbilical vein endothelial cells.

1.3 Detect Tube Formation of Human Umbilical Vein Endothelial Cells (HUVEC) Promoted by IDHP—Matrigel Gel Method Pipette tips and 96-well plate were pre-cooled at −20° C. Matrigel gel was placed on ice and melted, and then added to the pre-cooled 96-well plate (60 μl/well). Avoid the formation of air bubbles. The plate was placed on ice for 5 minutes to level the Matrigel gel, and then put into a cell culture incubator for 30 minutes to solidify. Endothelial cells were added to the wells ($5\times10^4$ cells/well) containing Matrigel gel, and fresh medium containing different concentrations of the drug was added, incubated at 37° C. for 8 hours. The plate was observed under a microscope, 5 fields of view were chosen at 0, 3, 6, 9 o'clock positions and the center of each well, the number of tubules and the integrity of the tubular structure were observed and images were acquired. The result shows that, compared with the Ctrl control group, IDHP significantly promoted the tube formation of primary human umbilical vein endothelial cells (HUVEC), indicating that IDHP has an activity of promoting angiogenesis in vitro.

Example 2 IDHP Promotes Angiogenesis in Transgenic Zebrafish

The transgenic Tg (VEGFR2:GFP) zebrafishes were cultured under the standard conditions of illumination for 14 hours/dark for 10 hours at 28° C. Healthy and mature zebrafishes were put into a breeding container at a ratio of female to male 1/1 or 1/2 for mating. The fertilized eggs were obtained at 9 to 10 o'clock the next day. The fertilized eggs were sterilized and washed, then transferred to zebrafish embryo culture medium and cultured at 28° C.

Drug solution was added to a 24-well culture plate, and 24 hpf embryos were carefully transferred to wells, 8-10 per well, and culture medium was added until a total volume of 2 ml to make sure that the final concentration of DMSO in the medium was not higher than 1%. After 24-hour drug treatment, the embryos were observed under a fluorescence microscope, and the total number of intersegmental vessels in trunk and tail were counted, and the relative generation rate of ISV in each administration group was calculated. Analysis of variance between groups was performed using SPSS software.

Figure 4:
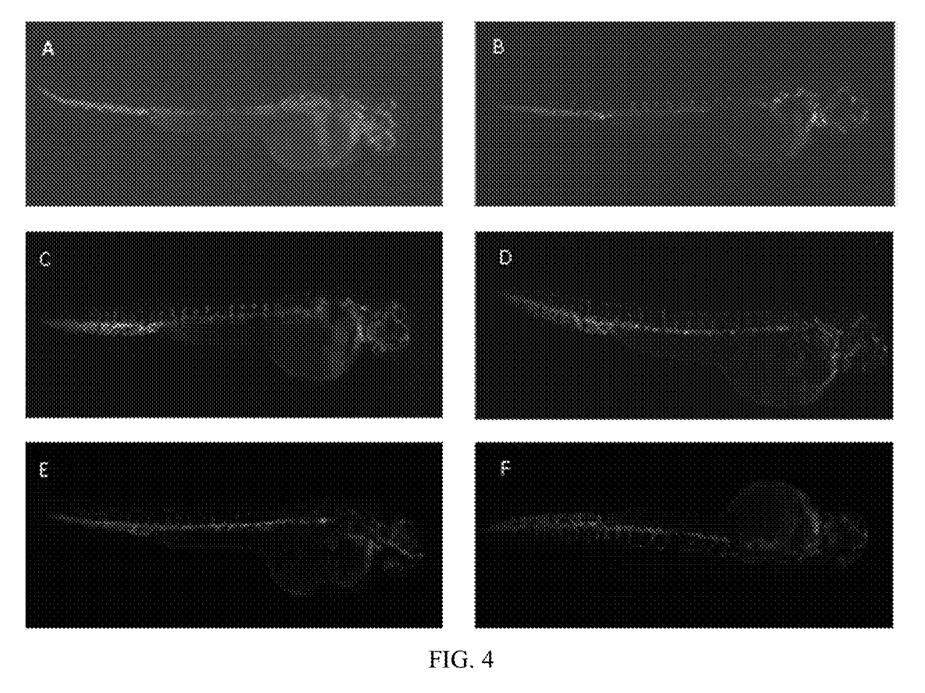
FIG. 4 shows the effect of IDHP on growth of zebrafish intersegmental vessels, wherein: A, PTK 787; B, 0.01 μM IDHP; C, 0.1 μM IDHP; D, 1.0 μM IDHP; E, 10.0 μM IDHP; F, 10 nM VEGF.
Figure 5:
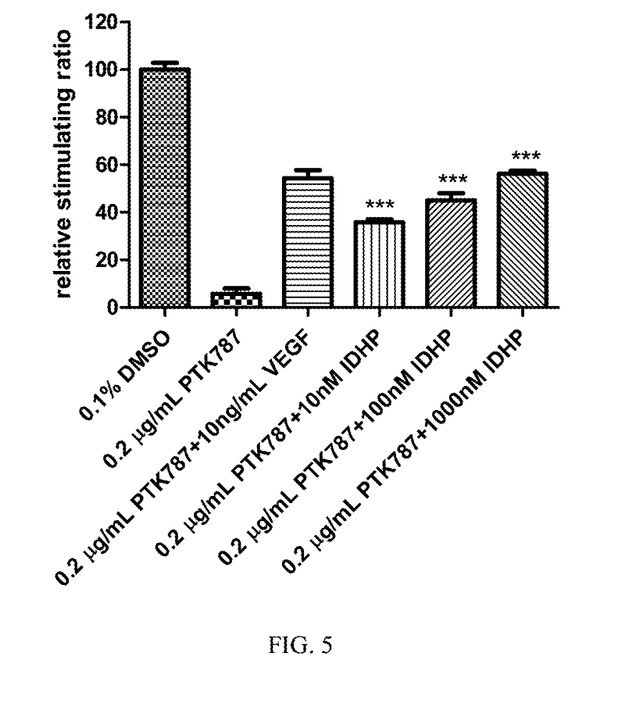
FIG. 5 shows the result of the growth of intersegmental vessels promoted by IDHP in zebrafish.

The result shows that IDHP at concentrations of 0.01, 0.1 and 1.0 μM, respectively, significantly promoted the growth of intersegmental vessels and posterior longitudinal blood vessels in zebrafish (FIG. 4) with a significant increase in the total number and length of blood vessels (Table 1). According to the formula: relative generation rate (%)=(total length of blood vessels in the drug treatment group−total length of blood vessels in the control group of PTK787)÷total blood pressure of normal control group×100, the relative generation rate was calculated, and the result showed a dose-dependent relationship of the drug treatment (FIG. 5).

TABLE 1

The Promotion Effect of IDHP on the Growth of Zebrafish ISV

| Name | Concentration | Length of Blood Vessels (μm) | Number of Blood Vessels |
|---|---|---|---|
| DMSO | 0.1% | 785.1 ± 49.5 | 28.9 ± 3.8 |
| PTK787 | 0.1 μg/ml | 36.4 ± 14.2 | 3.6 ± 1.3 |
| VEGF | 10 ng/ml | 420.0 ± 54.2 | 29.3 ± 3.3 |
| IDHP | 0.01 μM | 287.4 ± 18.8*** | 25.0 ± 8.6*** |
|  | 0.1 μM | 359.2 ± 58.2*** | 26.1 ± 3.3*** |
|  | 1.0 μM | 447.6 ± 19.5*** | 34.4 ± 7.0*** |

Note:
***represents p < 0.001 compared with the control

Example 3 IDHP Inhibits Normal Human Platelet Aggregation Induced by ADP and Collagen The whole blood samples of healthy volunteers were collected into the anticoagulant tubes and centrifuged at 800 g for 5 minutes at room temperature. The light yellow supernatant was the platelet-rich plasma (PRP); the remaining solution was further centrifuged at 4000 g for 10 minutes at room temperature, and the supernatant obtained was platelet-poor plasma (PPP).

Figure 6:
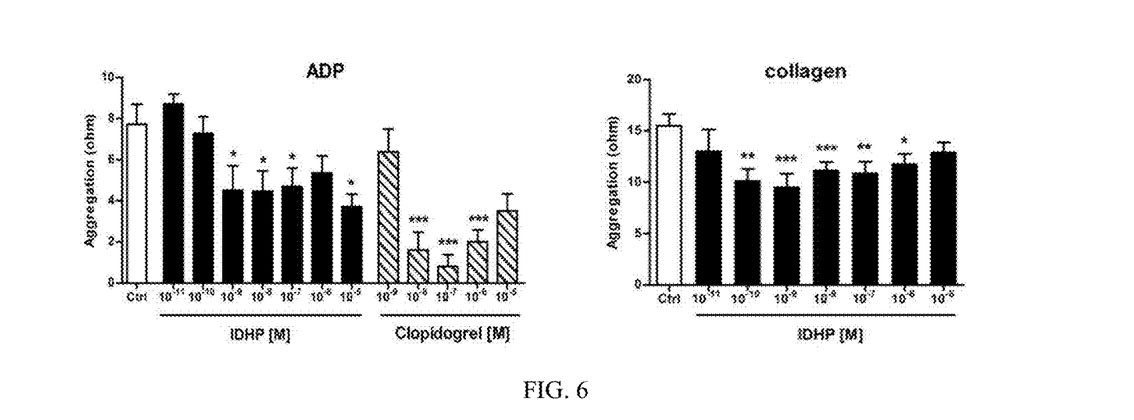
FIG. 6 shows the effect of IDHP on ADP and collagen-induced normal human platelet aggregation (n=16)

PRP was adjusted to $3\times10^5$ platelets/μl with PPP, 300 μl of adjusted PRP was added to 30 μl of PBS or different concentrations of IDHP and incubated at 37° C. for 3 minutes in a blood coagulation apparatus. Collagen or ADP at a final concentration of 3 μmol/L was added to initiate the aggregation reaction of platelets. The inhibitory effect of IDHP and clopidogrel on platelet aggregation was determined by turbidimetry. The result in FIG. 6 shows that clopidogrel significantly inhibited ADP-induced platelet aggregation in the measured concentration range (p<0.001); compared with ADP alone or collagen alone groups (Ctrl), IDHP respectively and significantly inhibit ADP- or collagen-induced platelet aggregation, and the inhibitory effect on collagen-induced platelet aggregation was more significant (P<0.001).

Example 4 Toxicological Study of IDHP 4.1 Acute Toxicity Test in Mice with Rapid Administration Sixty mice were used, half male and half female, and randomly divided into 6 groups. IDHP was formulated into six concentrations using physiological saline: 3.145%, 2.68%, 2.4%, 2%, 1.875% and 1.6%. The spacing between the concentrations was 1:0.9. After the animals were fasted for 12 hours, each group was subjected to IV administration, the volume was 20 ml/kg, and the administration was completed within 5 seconds for each animal. The doses of the six groups were 629 mg/kg, 530 mg/kg, 480 mg/kg, 400 mg/kg, 375 mg/kg, and 320 mg/kg, respectively. After the IV, the animal represented shortness of breath, rapid heartbeat, jumping and convulsions, followed by slow movement and lying on the ground. The poisoning phenomenon increased with the increase of the dose; the dead animals basically died within 1 minute after the administration, and the undead animals returned to normal after 10 minutes. The dead mice was subjected to autopsy, observed by naked eyes, there was no abnormality in the vital organs such as heart, liver, spleen, lung, kidney, brain, stomach or intestine, $LD_{50}$ was measured by the Bliss method and the value was 424±58 mg/kg, the 95% confidence interval was 370 to 486 mg/kg, as shown in Table

TABLE 2

$LD_{50}$ of IDHP Measured by Bliss's Method

| Dose mg/kg | Logarithmic Dose | Number of Animals | Mortality Rate (%) | Test Probability Unit | Regression Probability Unit | Error ($\times 10^{-6}$) |
|---|---|---|---|---|---|---|
| 629 | 2.798 | 10 | 100 | 6.96 | 7.24 | 2.13 |
| 530 | 2.724 | 10 | 100 | 6.96 | 6.26 | 2.53 |
| 480 | 2.681 | 10 | 50 | 5.00 | 5.7 | 2.77 |
| 400 | 2.602 | 10 | 40 | 4.75 | 4.66 | 3.19 |
| 375 | 2.574 | 10 | 40 | 4.75 | 4.3 | 3.34 |
| 320 | 2.505 | 10 | 0 | 3.04 | 3.4 | 3.72 |

Base Mortality Rate: 0%
Significance index: G = 0.1760 X50 = −0.3722 Sx = 0.0158 G is relatively small, omitted
Heterogeneity check: Chi2 = 6.90 Chi2.05 = 9.64 Sb = 2.7993 No heterogeneity
Regression Equation Formula: Y(Probit) = 9.8687 + 13.0795 × log(D) r = 0.8716 $LD_{50}$ = 424.4 ± 39.7 (mg/kg)
Feiller Heterogeneity Correction: Sx = 0.0229 Sb = 3.6778 $LD_{50}$ = 424.4 ± 57.9 (mg/kg) 95% confidence interval was 370.4 to 486.2 mg/kg.

4.2 Acute Toxicity Test in Mice with Slow Administration

After housing in the laboratory for 1 day, the test mice with qualified body weight were selected and randomly divided into groups according to body weight and sex, 10 for each group, half male and half female. According to the result of premeasurement, the absolute lethal dose was 2.4 g/kg. The mice were subjected to tail vein administration, the dose for the mice was calculated according to body weight. The doses were 2.4 g/kg, 2.2 g/kg, 2.0 g/kg, and 1.8 g/kg, respectively, and the drug delivery rate was calculated. The administration was completed within 10 minutes. The reactions of the mice were observed after the administration and the death of the mice was recorded within 14 days.

The main toxic reactions after intravenous administration were central inhibition, respiratory failure, etc. Most of the death occurred during the administration period. No abnormal changes were found in anatomy. After 14 days of observation, the mortality rate of the mice was calculated. $LD_{50}$ was measured by the Bliss method and the value was 2.048 g/kg±0.085 g/kg, 95% confidence limit was 1.965 to 2.135 g/kg, the result is shown in Table 3:

TABLE 3

$LD_{50}$ of IDHP Measured by Bliss's Method in Mice Administered via Tail Vein

| Group | Number of Mice | Dose (d) g/kg | Number of Deaths (n) | Mortality Rate (%) |
|---|---|---|---|---|
| 1 | 11 | 2.4 | 10 | 100 |
| 2 | 10 | 2.2 | 8 | 80 |
| 3 | 10 | 2.0 | 3 | 30 |
| 4 | 10 | 1.8 | 1 | 10 |

4.3 Hemolysis Assay

Arterial blood from domestic rabbit was collected, fibrin was removed, red blood cells were washed with physiological saline and then formulated into a 2% red blood cell physiological saline solution. The test was operated according to Table 4, four parallel test tubes in each group.

TABLE 4

| Group | Control Group | IDHP Group ($10^{-3}$ mol/l) | | | | |
|---|---|---|---|---|---|---|
| | | 2 | 4 | 6 | 8 | 10 |
| IDHP Solution (ml) | / | 0.1 | 0.2 | 0.3 | 0.4 | 0.5 |
| Physiological Saline (ml) | 2.5 | 2.4 | 2.3 | 2.2 | 2.1 | 2.0 |
| 2% red blood cell (ml) | 2.5 | 2.5 | 2.5 | 2.5 | 2.5 | 2.5 |

After the above operation, the tubes were put in water bath at 37±0.5° C., one tube from each group was taken at 0.5 h, 1 h, 2 h and 3 h respectively, centrifuged at 3000 rpm for 15 minutes. Red blood cell hemolysis was observed, at the same time, the morphology of red blood cells was observed under light microscope.

The test result shows that the red blood cells were intact, there was no obvious hemolysis, suggesting that IDHP has no hemolysis effect.

Example 5: Endogenous Study of IDHP

Lipase-catalyzed synthesis of IDHP from isopropanol and Danshensu.

Figure 7:
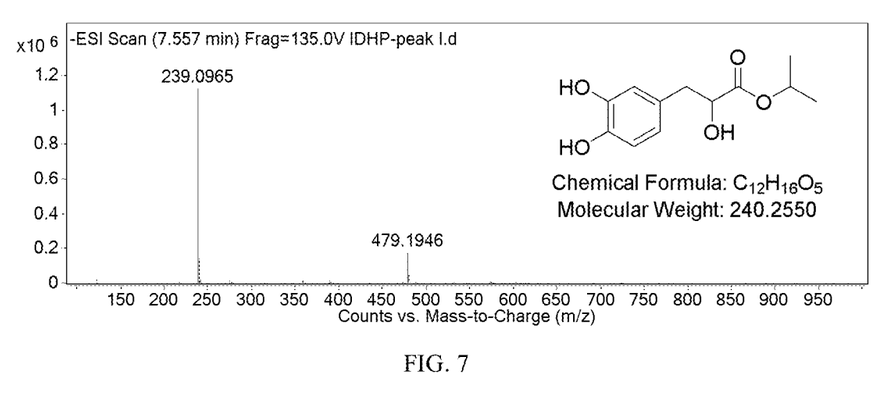
FIG. 7 shows the identification of IDHP by mass spectrum.
Figure 8:
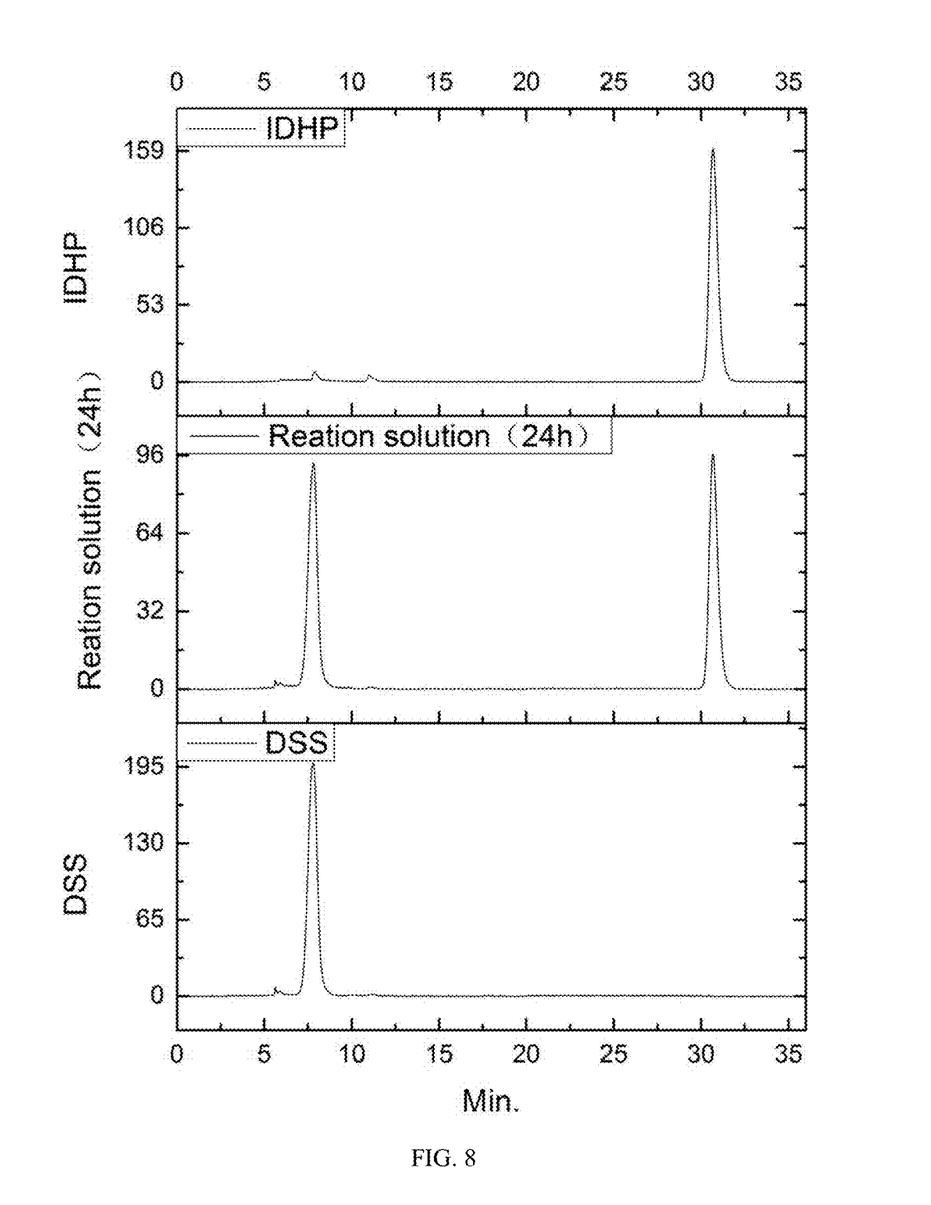
FIG. 8 shows the identification of IDHP by liquid chromatography.

For specific implementation, refer to but is not limited to the following solution:

Danshensu (5.0 mg, 0.025 mmol), isopropanol (0.3 mg, 0.005 mmol), water (1.5 ml) and lipase (5 mg) were sealed, put in a shaker (220 rpm) and incubated at 37° C. for 24 hours. 100 μl of the reaction solution was taken, added with 100 μl of ethyl acetate, and shaked for 20 seconds. The organic phase was subjected to liquid chromatography and mass spectrum. The mass spectrum result ([M-1]=239.0965) is shown in FIG. 7; the liquid chromatography result is shown in FIG. 8.

Liquid chromatography detection conditions were, methanol: 0.2% formic acid water=3:7; flow rate: 0.6 ml/min; chromatography column: C18 (zorbax), 250 mm, 5 μm, 4.6 mm (inner diameter); column temperature: 25° C.

Combined with the inventors' previous research in which it was found that Danshensu is a human body-derived substance, also, lipase widely presents in animals, plants and microorganisms (such as molds, bacteria) tissues containing fats, and human body contains isopropanol, suggesting that IDHP is an endogenous substance of human body.

Example 6: IDHP Emulsion

The emulsion formula was, IDHP: 10.0 g, vitamin E: 3.0 g, refined soybean: 200.0 g, oleic acid: 15.0 g, refined protein lecithin: 25.0 g, water for injection: about 900 ml, glycerol: 2.0 g.

Example 7: IDHP Dropping Pill

IDHP: 10.4 g, starch: 6.3 g, sodium carboxymethyl starch: 1.8 g, polyethylene glycol (molecular weight 6000): 26.5 g. During the preparation, prescription amount of IDHP and polyethylene glycol 6000 were heated to 80° C. to get melted, and then starch and sodium carboxymethyl starch were added, mixed well, dripped into liquid paraffin coolant (1 to 5° C.) to make 1000 pills, 45 mg per pill. Traces of oil on the surface were removed to obtain the final product.

The present disclosure has been described in detail above including its preferred embodiments. However, it should be understood that, considering what is disclosed in the present disclosure, a person having ordinary skill in the art can make modifications and/or improvements to the present disclosure within the spirit and scope of the invention, which also fall within the scope of the present disclosure.

The invention claimed is:

1. A method of preventing and treating a disease related to coronary artery atherosclerosis comprising administering β-(3,4-dihydroxyphenyl)-α-hydroxyisopropyl propionate (IDHP) to a subject in need thereof.

2. The method according to claim 1, wherein the disease related to coronary artery atherosclerosis is one or more selected from the group consisting of stroke, coronary heart disease and myocardial infarction.

3. A method of inhibiting platelet aggregation comprising administering IDHP to a subject in need thereof.

4. A method of promoting angiogenesis comprising administering IDHP to a subject in need thereof.

5. A method of preventing and treating vascular dementia comprising administering IDHP to a subject in need thereof.

6. The method according to claim 1, wherein IDHP is in a form of a medicament or a healthcare food.

7. The method according to claim 3, wherein IDHP is in a form of a medicament or a healthcare food.

8. The method according to claim 4, wherein IDHP is in a form of a medicament or a healthcare food.

9. The method according to claim 5, wherein IDHP is in a form of a medicament or a healthcare food.

* * * * *